(12) United States Patent
Labhasetwar et al.

(10) Patent No.: US 11,439,690 B2
(45) Date of Patent: Sep. 13, 2022

(54) METHODS OF TREATING SPINAL CORD INJURY

(71) Applicant: The Cleveland Clinic Foundation, Cleveland, OH (US)

(72) Inventors: Vinod Labhasetwar, Solon, OH (US); Hayder H. Jaffer, Rock River, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/766,449

(22) PCT Filed: Feb. 6, 2014

(86) PCT No.: PCT/US2014/015112
§ 371 (c)(1),
(2) Date: Aug. 6, 2015

(87) PCT Pub. No.: WO2014/124142
PCT Pub. Date: Aug. 14, 2014

(65) Prior Publication Data
US 2015/0374798 A1 Dec. 31, 2015

Related U.S. Application Data

(60) Provisional application No. 61/762,008, filed on Feb. 7, 2013.

(51) Int. Cl.
| A61K 38/44 | (2006.01) |
| A61K 9/00 | (2006.01) |
| A61K 9/19 | (2006.01) |
| A61K 9/51 | (2006.01) |

(52) U.S. Cl.
CPC .......... *A61K 38/446* (2013.01); *A61K 9/0019* (2013.01); *A61K 9/19* (2013.01); *A61K 9/5153* (2013.01); *A61K 38/44* (2013.01); *C12Y 111/01006* (2013.01); *C12Y 115/01001* (2013.01)

(58) Field of Classification Search
None
See application file for complete search history.

(56) References Cited

U.S. PATENT DOCUMENTS

| 6,123,956 A * | 9/2000 | Baker .................. A61K 9/0085 424/426 |
| 6,143,037 A | 11/2000 | Goldstein et al. |
| 6,814,980 B2 | 11/2004 | Levy et al. |
| 7,332,159 B2 | 2/2008 | Labhasetwar et al. |
| 7,727,554 B2 | 6/2010 | Labhasetwar et al. |
| 8,182,807 B2 | 5/2012 | Labhasetwar et al. |
| 8,507,437 B2 | 8/2013 | Labhasetwar |
| 8,865,216 B2 | 10/2014 | Labhasetwar et al. |
| 9,138,416 B2 | 9/2015 | Labhasetwar et al. |
| 10,016,488 B2 | 7/2018 | Labhasetwar et al. |
| 10,206,885 B2 | 2/2019 | Labhasetwar et al. |
| 10,517,934 B2 | 12/2019 | Labhasetwar |
| 2003/0059455 A1 | 3/2003 | Barkats et al. |
| 2003/0077564 A1 * | 4/2003 | Brewer ................ A61K 9/0085 435/1.1 |
| 2003/0118545 A1 * | 6/2003 | Shi ......................... A61K 31/00 424/78.37 |
| 2006/0067925 A1 | 3/2006 | Labhasctwar et al. |
| 2006/0127386 A1 * | 6/2006 | Muzykantov ........ A61K 9/5031 424/94.4 |
| 2006/0149089 A1 * | 7/2006 | Malfroy-Camine ........................ C07F 13/005 556/32 |

FOREIGN PATENT DOCUMENTS

| CA | 2839106 A1 | 1/2013 |
| JP | 2007/075058 | 3/2007 |
| WO | WO 00/54595 A1 | 9/2000 |
| WO | WO 02/092781 A2 | 11/2002 |
| WO | WO 03/029417 A2 | 4/2003 |

OTHER PUBLICATIONS

Kim, Y-t et al. 2009. Nanoparticle-mediated local delivery of methylprednisolone after spinal cord injury. Biomaterials. 30: 2582-2590. specif. pp. 2582, 2583, 2587, 2589.*

Akbarzadeh, A. et al. 2013. Liposome: classification, preparation, and applications. Nanoscale Research Letters 8(102): 1-9. specif. p. 1.*

(Continued)

*Primary Examiner* — Olivia M. Wise
*Assistant Examiner* — Sharon M. Papciak
(74) *Attorney, Agent, or Firm* — Casimir Jones, S.C.; Jason R. Bond

(57) ABSTRACT

The invention is directed to a method of treating a spinal cord injury, a neurodegenerative disease or a neuronal injury in an individual in need thereof comprising administering an effective amount of superoxide dismutase (SOD) and catalase to the individual, wherein the superoxide dismutase and the catalase are encapsulated in one or more nanoparticles that release the SOD and catalase upon administration. Another aspect of the invention is directed to compositions comprising superoxide dismutase (SOD) and catalase encapsulated in one or more nanoparticles.

18 Claims, 10 Drawing Sheets

(56) References Cited

OTHER PUBLICATIONS

Lim, K.H. et al. 1986. Prevention of reperfusion injury of the ischemic spinal cord: use of recombinant superoxide dismutase. Annals of Thoracic Surgery 42: 282-286. specif. pp. 282, 285.*
Nakauchi, K. et al. 1996. Effects of lecithinized superoxide dismutase on rat spinal cord injury. Journal of Neurotrauma 13(10): 573-582. specif. pp. 573, 574, 580.*
Ipek, G. et al. 1997. Intraaortic catalase administration to prevent spinal cord ischemia-reperfusion injury. GKD Cer. Derg. (Turkish Journal of Thoracic and Cardiovascular Surgery) 5: 83-87. see Eng. Abstract, p. 83.*
Ahn, Y. et al. 2004. Percutaneous endoscopic lumbar discectomy for recurrent disc herniation: surgical technique, outcome, prognostic factors of 43 consecutive cases. Spine 29(16): E326-E332. specif. p. E326.*
English machine translation.Ipek, G. et al. 1997. Intraaortic catalase administration to prevent spinal cord ischemia-reperfusion injury. GKD Cer. Derg. (Turkish Journal of Thoracic and Cardiovascular Surgery) 5: 83-87. Full article.*
Jia, Z. et al. 2012; published online Oct. 11, 2011. Oxidative stress in spinal cord injury and antioxidant-based intervention. Spinal Cord 50: 264-274. specif. 264, 265.*
Bonfoco, E. et al. 1995. Apoptosis and necrosis: two distinct events induced, respectively, by mild and intense insults with N-methyl-D-aspartate or nitric oxide/superoxide in cortical cell cultures. Proceedings of the National Academy of Sciences (PNAS) 92: 7162-7166. specif. p. 7162.*
Wang, Y.-C. et al. 2008. Sustained intraspinal delivery of neurotrophic factor encapsulated in biodegradable nanoparticles following contusive spinal cord injury. Biomaterials 29: 4546-4553. specif. pp. 4546, 4547, 4548.*
Bertram, J.P. et al. 2009. Intravenous hemostat: nanotechnology to halt bleeding. Science Translational Medicine 1(11): 1-8. specif. pp. 1, 2.*
DeVivo, M.J. 1997. Causes and costs of spinal cord injury in the United States. Spinal Cord 35: 809-813; specif. p. 809.*
Garrison, H.G.et al. 2012. Paramedic skills and medications: practice options utilized by local advanced life support medical directors. Published online by Cambridge University Press. Retrieved on Sep. 14, 2021. Downloaded from: <https: see document for complete download address> pp. 1-3; specif. p. 1.*
Hall, E.D. 2011. Antioxidant therapies for acute spinal cord injury. The American Society for Experimental NeuroTherapies, Inc. 8: 152-167; specif. pp. 152, 158, 159, 160, 161, 162.*
Chang, T.M.S., et al., "Two Future Generations of Blood Substitutes Based on Polyhemoglobin-SOD-Catalas and Nanoencapsulation," *Advanced Drug Delivery Reviews*, 40(3): 213-218 (2000).
Dziubla, T.D., et al., "Polymer Nanocarriers Protecting Active Enzyme Cargo Against Proteolysis," *Journal of Controlled Release*, 102(2): 427-439 (2005).
Hood, E., et al., "Nanocarrier for Vascular Delivery of Antioxidants," *Nanomedicine (Lond)*, 6(7): 1257-1272 (2011).
Hu, P., et al., "Scavenging ROS: Superperoxide Dismutase/Catalase Mimetics by the Use of an Oxidation-Sensitive Nanocarrier/Enzyme Conjugate," *Bioconjugate Chem.*, 23(3): 438-449 (2012).
Jaffer, H., et al., "Advances in Stroke Therapy," *Drug Deliv. and Transl. Res.*, 1(6): 409-419 (2011).
Klyachko, N.L., et al., "Cross-Linked Antioxidant Nanozymes for Improved Delivery to CNS," Nanomedicine: *Nanotechnology, Biology and Medicine*, 8(1): 119-129 (2012).
Labhasetwar, V.D., "Project Information—1R01NS070896-01—Details," http://projectreporter.nih.gov/project_info_details.cfm?aid=7943566&icde=0 [Retrieved on Aug. 6, 2015].
Labhasetwar, V.D., "Project Information—1R01NS070896-01," http://projectreporter.nih.gov/project_info_description.cfm?projectnumber=1R01NS070896-01 [Retrieved on Aug. 6, 2015].
Manickam, D.S., et al., "Well-Defined Cross-Linked Antioxidant Nanozymes for Treatment of Ischemic Brain Injury," *Journal of Controlled Release*, 162(3): 636-645 (2012).
Reddy, M.K., et al., "Nanoparticle-Mediated Delivery of Superoxide Dismutase to the Brain: An Effective Strategy to Reduce Ischemia-Reperfusion Injury," *FASEB J.*, 23(5): 1384-1395 (2009).
Reddy, M.K., et al., "Superoxide Dismutase-Loaded PLGA Nanoparticles Protect Cultured Hunan Neurons Under Oxidative Stress," *Appl. Biochem. Biotechnol.*, 151 (2-3): 565-577 (2008).
Singhal, A., et al., "Nanoparticle-Mediated Catalase Delivery Protects Human Neurons from Oxidative Stress," *Cell Death and Disease*, 4(11): e903 (2013).
Uttara, B., et al., "Oxidative Stress and Neurodegenerative Diseases: A Review of Upstream and Downstream Antioxidant Therapeutic Options," *Current Neuropharmacology*, 7(1): 65-74 (2009).
Notification of Transmittal of the International Search Report and the Written Opinion of the International Searching Authority, PCT Application No. PCT/US2014/015112, entitled "Methods of Treating Spinal Cord Injury", dated Jan. 26, 2015.
Notification Concerning Transmittal of International Preliminary Report on Patentability, PCT Application No. PCT/US2014/015112, entitled "Methods of Treating Spinal Cord Injury", dated Aug. 20, 2015.
Andrabi et al., "Nanoparticles with antioxidant enzymes protect injured spinal cord from neuronal cell apoptosis by attenuating mitochondrial dysfunction," J Control Release, 317 (2020) 300-311.
Adjei, et al., "Heterogeneity in nanoparticles influences biodistribution and targeting," Nanomedicine (Lond). Feb. 2014; 9(2): 267-278.
Adjei, et al., "Inhibition of bone loss with surface-modulated, drug-loaded nanoparticles in an intraosseous model of prostate cancer," Journal of Controlled Release 232 (2016) 83-92.
Aslam et al., "Polyvinyl Alcohol: A Review of Research Status and Use of Polyvinyl Alcohol Based Nanocomposites," Polymer Engineering and Science, 2018, pp. 2119-2132.
Fang et al., "Cleavable PEGylation: a strategy for overcoming the "PEG dilemma" in efficient drug delivery," Drug Delivery, 2017, vol. 24, No. 2, pp. 22-32.
Jang et al., "Preparation of Biodegradable PLGA Nanospheres Employing a Fast Solvent Evaporation Method," J. Ind. Eng. Chem., vol. 13, No. 6, 2007, pp. 1043-1046.
Panyam et al., "Rapid endo-lysosomal escape of poly(DL-lactide-co-glycolide) nanoparticles: implications for drug and gene delivery," FASEB J., vol. 16, 2002 pp. 1217-1226.
Sahoo et al., "Residual polyvinyl alcohol associated with poly (D,L-lactide-co-glycolide) nanoparticles affects their physical properties and cellular uptake," Journal of Controlled Release, 82, 2002, pp. 105-114.
Verhoef et al., "Questioning the Use of PEGylation for Drug Delivery," NIH Public Access, Drug Deliv. Transl. Res. Dec. 2013, 3(6), pp. 499-503.
Yoneki et al., "One-pot facile preparation of PEG-modified PLGA nanoparticles: Effects of PEG and PLGA on release properties of the particles," Colloids and Surfaces A: Physicochemical and Engineering Aspects, 469, 2015, pp. 36-72.
Zhang et al., "PEG-PLGA copolymers: Their structure and structure-influenced drug delivery applications," Journal of Controlled Release, 183, 2014, pp. 77-86.
Duan et al., "Nrf2 activity is lost in the spinal cord and its astrocytes of aged mice," In Vitro Cell. Dev. Biol. Animal (2009) 45:388-397.
Lucas et al., "Effect of Glutathione Augmentation on Lipid Peroxidation after Spinal Cord Injury," Journal of Neurotrauma, vol. 19, No. 6, 2002; pp. 763-775.

* cited by examiner

Healing of Spinal Cord at 28 days

Untreated

Treated

Syringomyelia (Cavitations)

Untreated

Treated

Migration of Microglia: Role in Repair Process

6 Days

28 Days

METHODS OF TREATING SPINAL CORD INJURY

RELATED APPLICATION

This application is the U.S. National Stage of International Application No. PCT/US2014/015112, filed Feb. 6, 2014, which designates the U.S., published in English, and claims the benefit of U.S. Provisional Application No. 61/762,008, filed Feb. 7, 2013. The entire teachings of the above applications are incorporated herein by reference.

GOVERNMENT SUPPORT

This invention was made with government support under Army Grant #W81XWH-16-1-0786 awarded by the U.S. Department of Defense and NS092033 awarded by the National Institutes of Health. The government has certain rights in the invention.

BACKGROUND OF THE INVENTION

Spinal cord injury (SPI) has devastating effects on those affected with SPI for the rest of their life. According to the Christopher & Dana Reeve Foundation, more than million people in the U.S. are living with paralysis due to SPI. Patients with SPI also suffer from other serious health complications such as impaired bladder function, cardiac disorders, hypotension, etc. The costs of living with SPI are considerable, and this condition also affects the lives of close family members. It is estimated that SPI cost the healthcare industry $40.5 billion annually. Despite advances in medical and surgical care, current clinical therapies for SPI are limited. The major impediment is to facilitate the repair of the injured spinal cord and regain neuronal connectivity.

Thus, a need exists for improved methods of treating SPI.

SUMMARY OF THE INVENTION

Regeneration of injured spinal cord leading to resumption of locomotive functions and neurological recovery is shown herein in a rat model of traumatic SPI. Specifically, the treatment involves administration of antioxidant enzymes (e.g., a single-dose intravenous injection) superoxide dismutase (SOD) and catalase in nanoparticles (e.g., nano-SOD/catalase).

Accordingly, in one aspect, the invention is directed to a method of treating a spinal cord injury in an individual in need thereof comprising administering an effective amount of superoxide dismutase (SOD) and catalase to the individual, wherein the superoxide dismutase and the catalase are encapsulated in one or more nanoparticles that release the SOD and catalase upon administration.

In another aspect, the invention is directed to a method of treating a neurodegenerative disease or a neuronal injury in an individual in need thereof wherein the neurodegenerative disease or the neuronal injury is associated with excessive production of one or more reactive oxygen species (ROS), comprising administering an effective amount of superoxide dismutase and catalase to the individual, wherein the superoxide dismutase and the catalase are encapsulated in one or more nanoparticles.

In another aspect, the invention is directed to a method of protecting a spinal cord in an individual in need thereof during a medical intervention (spinal cord surgery, back/neck surgery) comprising administering an effective amount of superoxide dismutase and catalase to the individual, wherein the superoxide dismutase and the catalase are encapsulated in one or more nanoparticles.

Another aspect of the invention is directed to compositions comprising superoxide dismutase (SOD) and catalase encapsulated in one or more nanoparticles. In one aspect, the SOD and the catalase are encapsulated in separate nanoparticles. In another aspect, the SOD and catalase are encapsulated in the same nanoparticle, that is, each of the nanoparticles comprise the SOD and the catalase.

DETAILED DESCRIPTION OF THE INVENTION

Figure 1:
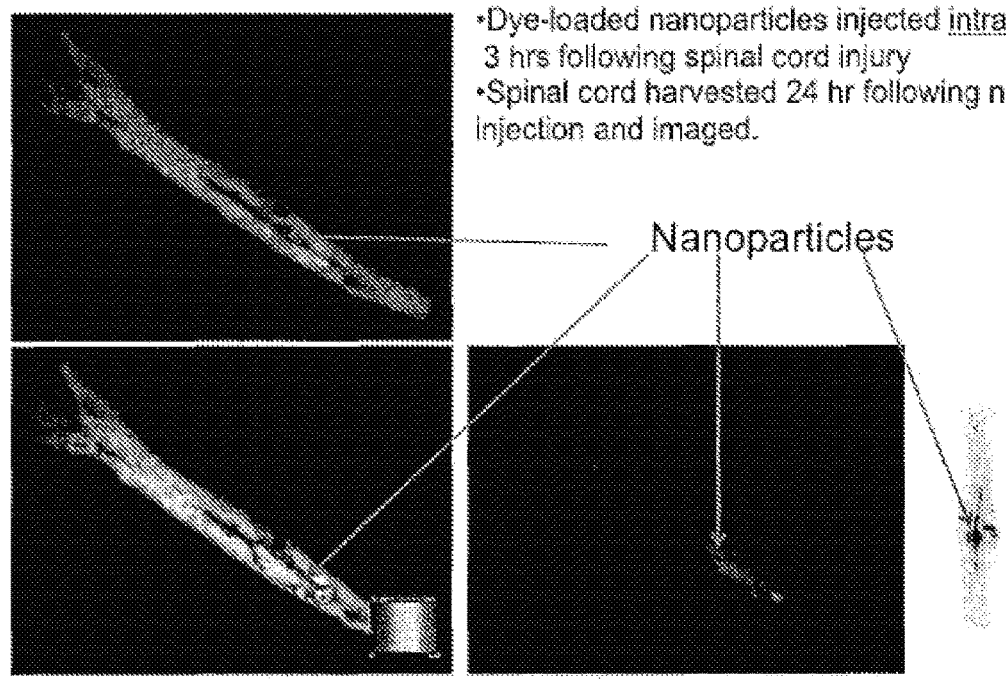
FIG. 1 shows nanoparticle localization in the injured segment of spinal cord. Dye-loaded nanoparticles were injected intravenously 3 hours (hrs) following spinal cord injury. Spinal cord was harvested 24 hr following nanoparticle injection and imaged.

Described herein are methods that prevent damage and/or further deterioration and damage of a spinal cord by inhibiting the formation of reactive oxygen species (ROS). With a decrease in the production of ROS, inflammation is controlled thus allowing the injured spinal cord an opportunity to regain and revive its lost functionality. The compositions and methods described herein thus facilitate the overall recovery while also improving the functional and physiological recovery of the animal.

Specifically, the treatment involves administration of antioxidant enzymes (e.g., a single-dose intravenous injection) superoxide dismutase (SOD) and catalase in nanoparticles (NPs). In one aspect, SOD and catalase are administered in one or more NPs (e.g., nano-SOD/catalase). In a particular aspect, the SOD and catalase are formulated in NPs with an FDA approved biodegradable polymer and designed to release the encapsulated antioxidant enzymes in their active forms over a sustained period of time. The overall therapeutic strategy described herein minimized the secondary damage post-traumatic SPI, prevented activation of the inflammatory process, sustained the protective effects of antioxidant enzymes over time and created conditions favorable to facilitating the injured spinal cord repair. Mutilation by the primary injury is inevitable, however, as shown herein, the delayed response of the secondary injury offers an opportunity for therapeutic intervention. Nano-SOD/catalase, because of its ability to provide a sustained protective effect, prevented apoptosis of neurons that survived the primary injury, thus greatly reducing and delaying the subsequent inflammatory response.

As described herein, nano-SOD/catalase likely promote the phagocytic clearance of the damaged tissue resulting from the primary injury, an important process in tissue repair that is facilitated only in the absence of oxidative stress. The inhibition of inflammation in stimulating functional recovery and structural repair is limited due to hostile conditions in the injured spinal cord and/or brain. Nano-SOD/catalase thus create a pro-regenerative microenvironment by inhibiting ROS mediated damage and exerting anti-apoptotic and anti-inflammatory mechanisms.

A primary injury to the spinal cord can occur, for example, from a direct impact of a mechanical force on the spinal cord followed by the secondary injury which is usually accompanied by changes in the pathophysiological aspects of the spinal tissue. While it is impossible to forestall the primary injury, as shown herein the secondary injury which is more progressive in its path, provides a therapeutic window to treat and prevent the further extension the secondary damage. ROS formation occurs as a consequence of the secondary injury and continues to escalate and intensify the secondary injury process by causing enormous damage to cells, DNA, lipids, proteins and eventually causing cell death. At present, no effective neuroprotective pharmacological treatment exists that can prevent, minimize or halt the progression of such a protracted and devastating injury. Provided herein are methods of treating SPI and neurodegenerative diseases or neuronal injury using the antioxidant enzymes catalase and superoxide dismutase loaded into nanoparticles (NP) (e.g., biodegradable polymer-based NP (nano-SOD/catalase)) to neutralize the damaging effect of ROS and impede the formation of ROS and provide continual neuroprotection in traumatic SPI. In a particular aspect, the course of action of the nano-SOD/catalase is localization in the spinal tissue followed by initially rapid and later slow release of the encapsulated enzymes over a sustained period of time. This gradual and steady release of beneficial enzymes prevented auxiliary degeneration of the spinal tissue and averted subsequent motor function deterioration. Favorable conditions were created that allowed the natural repair mechanisms of the spine to restore and heal the impaired areas, allowing for an improved recovery of physiological, psychological and behavioral aspects of the affected individual. Antioxidants by themselves do not exhibit a sustained release activity for extensive time periods due to their instability and quick eradication from the body. Nano-SOD/catalase, with its ability to stay confined in the damaged tissue whilst providing a continual source of the therapeutic antioxidant enzymes, overcomes the above shortcoming.

Accordingly, in one aspect, the invention is directed to a method of treating a spinal cord injury in an individual in need thereof comprising administering an effective amount of superoxide dismutase (SOD) and catalase to the individual, wherein the superoxide dismutase and the catalase are encapsulated in one or more nanoparticles that release the SOD and catalase upon administration.

In another aspect, the invention is directed to a method of treating a neurodegenerative disease or a neuronal injury in an individual in need thereof wherein the neurodegenerative disease or the neuronal injury is associated with excessive production of one or more reactive oxygen species (ROS), comprising administering an effective amount of superoxide dismutase and catalase to the individual, wherein the superoxide dismutase and the catalase are encapsulated in one or more nanoparticles.

Examples of a neurodegenerative disease that is associated with excessive production of one or more reactive oxygen species ROS include Parkinson's Disease, Alzheimer's Disease, Multiple Sclerosis (MS), or Amyotrophic Lateral Sclerosis (ALS).

Examples of a neuronal injury that is associated with excessive production of one or more ROS include a traumatic brain injury (a brain injury due to an impact, vibration, fall (e.g., blast-associated traumatic brain injury), a spinal injury or a stroke.

In another aspect, the invention is directed to a method of protecting a spinal cord in an individual in need thereof during a medical intervention (spinal cord surgery, back/neck surgery) comprising administering an effective amount of superoxide dismutase and catalase to the individual, wherein the superoxide dismutase and the catalase are encapsulated in one or more nanoparticles. Examples of medical interventions include a surgical procedure involving the neck or back of the individual to treat one or more herniated discs, a spinal fusion, a spinal stenosis or a combination thereof. One can inject nano-SOD/catalase prior to intervention to minimize the damaging effect that can occur during the surgical procedure.

Another aspect of the invention is directed to compositions comprising superoxide dismutase (SOD) and catalase encapsulated in one or more nanoparticles. In one aspect, the SOD and the catalase are encapsulated in separate nanoparticles. In another aspect, the SOD and catalase are encapsulated in the same nanoparticle; that is, each of the nanoparticles comprises the SOD and the catalase.

An estimated 2.5 million people all over the world are victims of spinal cord injury (SPI), with about 12,000 new cases in the United States alone. It is estimated that $40.5 billion is expended annually for their care. SPI are commonly observed in younger populations ranging from ages 15-35 and most frequently occur in men. The elderly population is also a victim of SPI. The leading cause of paralysis is stroke (29 percent), followed by SPI (23 percent) and multiple sclerosis (17 percent). Data indicate that 1,275,000 people (0.4% US population) in the United States are living with SPI. As used herein an SPI refers to any injury to the spinal cord of an individual. Traumatic SPI refers to any form of physical trauma that can crush or compress the vertebrae causing irreparable impairment to the underlying spinal cord. An SPI may be caused by sudden falls, vehicle accidents, sports, impact, or violence. The location and intensity of the injury determine the symptoms that follow. These symptoms range from paralysis, pain, loss of sensation to incontinence and loss of sexual function. SPI severely debilitates the quality of life of the individuals affected physically and psychologically and also substantially impacts the social and economic state of the affected family.

The spinal cord is network of nerve fibers and cells that originate from the brain and form a part of the central nervous system (CNS). The vertebral column encapsulates the spinal cord and provides it with the necessary protection and shielding against any physical damage. The primary function of the spinal cord is to transmit neural signals/messages between the brain and the remaining body. The spinal cord also functions as a coordinating center for nerve reflexes. Apart from the protection rendered by the vertebral column, the spinal cord is protected by three layers of additional tissue, called spinal meninges. The outermost layer, known as the dura mater forms a protective tough coating while the arachnoid mater constitutes the middle protective coating and the pia mater refers to the innermost delicate layer. The epidural space refers to the space between the dura and the surrounding vertebrae which is filled with adipose tissue and also contains a network of blood vessels. The region between the arachnoid and the underlying pia mater makes up the subarachnoid space which contains the cerebrospinal fluid (CSF). A cross-section of the peripheral region of the spinal cord reveals two distinct sections, the white matter which contains the sensory and motor neurons, and the gray matter which is made up of nerve cell bodies. Ventricles from the brain, carrying CSF, extend all the way down to the center of the spinal cord to form the central canal. The spinal cord does not have a central artery that supplies it with blood. Instead it is supplied by three arteries that run along its length, known as the vertebral arteries, and many other smaller sporadically derived segmental arteries, known as the radicular arteries. This blood supply is severely compromised with trauma to the spinal cord and is often the most significant biological marker of the pathological injury cascade.

The primary pathological injury arises due to a direct impact of the physical/mechanical force and hence serves as the first predictive indicator of the severity or extent of the damage caused. The initial mechanical damage initiates a secondary cascade of cellular, biochemical and vascular events which further impair the primary damage. The primary damage causes a hemorrhage at the epicenter of the spinal cord and slowly traverses to the gray matter, which is highly vascularized, and later to the white matter, causing further neuronal degeneration. In fact, the natural response of the spinal cord can be categorized into three stages: acute, which occurs seconds to minutes after the injury, sub-acute, which occurs minutes to weeks after the injury, and chronic, which persists for months to years after the injury. Inflammation is the first immune mediated response of the spinal cord and occurs immediately after the injury, and can continue for up to several weeks or months after the injury. Four major types of immune cells are involved in the inflammation process. The first cells to arrive at the injury site are neutrophils which remain there for about 12 hours. T-cells arrive about 3 days later and are responsible for regulating the immune response. Microglia, the inherent immune cells, reside in the central nervous system (CNS). Monocytes arrive later at the injury site and differentiate into macrophages. These cell types are responsible for the release of various cytokines and free radicals which further activate other pro-inflammatory and glial cells, thus assisting in the enlargement and destruction of the primary injury. This systemic inflammatory response, mediated by primed neutrophils, begins within the circulation and leads to progressive secondary damage at the lesion site. Production of the reactive oxygen species (ROS) increases, causing oxidative damage to proteins, nucleic acids and lipids. ROS formation leads to the release of other pro-inflammatory cytokines and activates the matrix metalloproteinases which ultimately degrade and destroy the spinal cord tissue. Excitotoxicity by elevated levels of glutamate causes demyelination of axons and loss of neurons at the injury site, leading to either delays or blocks in the transmission of neuronal information, thus impairing the sensory and motor deficits. Severe hemorrhage in the gray matter leads to cell death in the acute phase due to necrosis and hours later due to apoptosis. Immediate ischemia at the site of the injury causes changes in the microcirculation patterns and chromatolysis, both representatives of cells with variation in circulation, ultimately causing neuronal cell death and conduction block. Cavitation occurs at the site of injury and progresses to form a much larger scar encapsulated crater which ultimately leads to glial scarring. Changes occur in the regulation patterns of the ions and an increased calcium influx is observed which lead to membrane breakdown, changes in gene expression and mitochondrial damage. Neurogenic shock may also be observed because of hypotension, bradycardia and hypothermia, which further worsens the existing condition. In case of SPI, all the above mechanisms are intricately intertwined in such a way that one propagates the other which eventually incapacitates the health of individual affected.

Primary physical trauma damages the spinal cord tissue and the secondary mechanisms further extend the damage to the rostral and caudal sections of the spinal cord. An important component of the secondary injury cascade is the generation of reactive oxygen species (ROS) such as superoxides, hydrogen peroxide, hydroxyl radicals, nitric oxide and peroxynitrite. Under physiological conditions, endogenous antioxidants, including superoxide dismutase, glutathione peroxidase and catalase, prevent oxidative damage. Superoxide dismutase (SOD) catalyzes the conversion of superoxide to hydrogen peroxide, which is further degraded by glutathione peroxidase and catalase (CAT) to molecular oxygen and water.

After SPI, ROS production exceeds the production capacity of the endogenous antioxidant system and the resulting "oxidative stress" can significantly modify neuronal functioning, leading to irreversible damage to lipid membranes and proteins. Due to a high concentration of unsaturated fatty acid side chains in membranes, the CNS is more susceptible to oxidative damage. Due to the inability of the mitochondria to carry out cellular respiration, there is a marked decrease in the ATP synthesis and a boost in the production of superoxide anions as well as their conversion to other free radicals. Oxidative stress produced due to ischemia and inflammation, activates cell death cycles by inducing apoptosis via irreversible oxidation of proteins, lipids and nucleic acids. Neutrophils, microglia and macrophages produce superoxide anion and nitric oxide which combine to form peroxynitrate which is highly reactive and toxic to the cells. Neutrophils, when activated undergo respiration producing superoxide anion, hydrogen peroxide ($H_2O_2$), hypochlorous acid and hydroxyl radicals. The enzymes that are involved in the process include, SOD which converts superoxide anion to $H_2O_2$ and myeloperoxidase which converts the $H_2O_2$ to hypochlorous acid. Together they damage the surrounding cells and neurons by lipid peroxidation and osmotic imbalance. Macrophages and microglia can also be induced to produce an oxidative burst that can release ROS into the tissue. Glutamate mediated excitotoxicity leads to an increase in intracellular calcium and the subsequent induction of enzymes, such as nitric oxide synthase and xanthine oxidase, that produce free radicals. All these processes kindle a complex cascade that increases neuroexcitotoxicity and neuronal vulnerability to subsequent damage. ROS have been shown to be responsible for loss in tissue function, advanced tissue disintegration and neuronal cell death.

A variety of spinal cord injuries can be treated using the methods and compositions provided herein. For example, the spinal cord injury can be a recent spinal cord injury or an existing spinal cord injury. In another aspect, the SOD and the catalase are administered upon or after removal of scar tissue from an existing spinal cord injury in the individual.

As discussed herein, SOD is an enzyme that catalyzes the conversion of superoxide to H2O2 and catalase is an enzyme that further degrades H2O2 to molecular oxygen and water. The SOD and catalase for use in the methods and compositions of the invention can be obtained from a variety of sources. In a particular embodiment, the SOD and/or catalase are mammalian SOD and/or mammalian catalase, and/or recombinant catalase. As used herein "mammal" and/or "mammalian" refer to a primate, canine, feline, rodent, and the like. Specific examples of mammalian SOD and/or catalase include human, pig, dog, cat, horse, cow, sheep, goat, rabbit, guinea pig, rats and mice SOD and/or catalase.

In particular embodiments, isolated SOD and/or catalase is used in the methods and compositions of the present invention. As used herein, "isolated", "purified", "substantially pure or purified" or "substantially isolated" refers to SOD and/or catalase (e.g., mammalian SOD and/or catalase) that is separated from the complex cellular milieu in which it naturally occurs, or chemical precursors or other chemicals when chemically synthesized. In some instances, the isolated or purified SOD and/or catalase comprises, consists essentially of, or consists of SOD and/or catalase or combinations thereof. Preferably, isolated or purified SOD and/or catalase comprises at least about 50%, 55%, 60%, 65%, 70%, 75%, 80%, 85%, 90%, 95%, 98% or 99% (on a molar basis) of all macromolecular species present. Modified enzymes such as PEGylated or conjugated to peptides such as TAT peptide could also be encapsulated in nanoparticles.

In the methods and compositions of the present invention, the SOD and catalase are encapsulated in one or more nanoparticles (NPs). A NP is a microscopic particle whose size is measured in nanometers (nm). Nanoparticles are below micron size, typically in the size range of 100 to 300 nm in diameter. As will be appreciated by those of skill in the art, a nanoparticle can be a particle less than about 1 nm, a particle of about 1 nm, a particle of less than about 100 nm, or larger particles such as greater than about 500 nm. The size of the nanoparticle will depend upon a variety of factors, which include, for example, the indication for which it is being used and the individual to whom it is being administered.

In particular aspects, the nanoparticle is biodegradable. In other aspects, the NPs are porous so that the ROS can diffuse into nanoparticles and becomes neutralized. Or encapsulated enzymes are released to neutralize ROS in the tissue. The effect could be due to the combination of the above two mechanisms i.e., diffusion of ROS into NPs and release of enzymes from NPs to neutralize ROS.

As will be appreciated by those of skill in the art, the NPs for use in the methods and compositions provided herein can be made from a variety of compounds. In a particular aspect, the NP is a polymer-based nanogel. Examples of suitable polymers include poly (D,L-lactide co-glycolide) (PLGA), polylactide (PLL), modifications of these polymers (e.g. polyethylene glycol) or a combination thereof.

As will also be appreciated by those of skill in the art, the NPs can comprise further components. For example, the polymer-based nanogel comprises polyvinyl alcohol and/or L-tartaric acid dimethyl ester.

The amount of SOD and catalase that can be loaded into the NPs will vary depending upon a variety of factors such as the condition/disease for which the SOD and catalase are being administered, the condition of the individual (e.g., health, age, weight, severity of the condition/disease, etc.) and the like. In one aspect, each of the one or more nanoparticles comprising SOD is loaded with about 10 μg to about 150 μg SOD. In other aspects, each of the one or more NPs are loaded with about 10, 20, 30, 40, 50, 60, 70, 80, 90, 100, 110, 120, 130, 140, 150, 160, 170, 180, 190, or 200 μg SOD. In another aspect, each of the one or more nanoparticles comprising catalase is loaded with about 10 μg to about 150 μg catalase. In other aspects, each of the one or more NPs are loaded with about 10, 20, 30, 40, 50, 60, 70, 80, 90, 100, 110, 120, 130, 140, 150, 160, 170, 180, 190, or 200 μg catalase.

In particular aspects, the NPs comprising SOD and catalase are formulated such that after administration, some of the SOD and the catalase is released rapidly from the one or more nanoparticles, and then the SOD and the catalase that remains in the one or more nanoparticles is released slowly over a sustained period of time. For example, enzymes at the nanoparticle interface are released first at a faster rate, which is typically referred to as a burst phase or release. After this initial release, the remaining enzymes are released slowly as the nanoparticle breaks down. Burst release can take place over 1-3 days and release of the remaining enzymes occurs over several weeks. In a particular aspect, release of the remaining enzymes occurs over 4-6 weeks.

The SOD and the catalase can be encapsulated in separate nanoparticles. Alternatively, each of the nanoparticles can comprise SOD and catalase (each nanoparticle can comprise both SOD and catalase).

The SOD and the catalase can be administered simultaneously or sequentially. In a particular aspect, the SOD and the catalase are administered simultaneously (e.g., as a single dose) to an individual. In another aspect, first the catalase is administered to the individual, then the SOD is administered to the individual. In yet another aspect, first the SOD is administered to the individual, then the catalase is administered to the individual.

In the methods of the invention in which the SOD and catalase are administered sequentially, the period of time between administration of the catalase and SOD will vary and can occur immediately, over several minutes, hours, days, weeks, months, years etc. after a spinal cord injury, the occurrence of a neurodegenerative disease or a neuronal injury. In addition, one or more excipients (vehicles) can be administered in between the sequential dose(s) of SOD and catalase. In a particular aspect, one or more excipients are administered after the catalase is administered and before the SOD is administered to the individual. In another aspect, one or more excipients are administered after the SOD is administered and before the catalase is administered to the individual. A variety of excipients can be used. Examples of excipients include water, saline, cornstarch, lactose, talc, magnesium stearate, sucrose, gelatin, and calcium stearate.

As will be appreciated by those of skill in the art, a variety of routes can be used to deliver the NPs comprising SOD and catalase. Such routes include, but are not limited to, intradermal, intramuscular, intraperitoneal, intraocular, intravenous, intra-arterial, subcutaneous, topical, oral, intranasal and local routes of administration. In a particular aspect, the SOD and the catalase are administered intravenously or administered locally at or near the spinal cord injury. For example, the NPs comprising SOD and catalase can be administered via carotid artery to aorta and/or into the ventricle of the heart to reduce the liver uptake of the injected nanoparticles.

The method and compositions of the invention can further comprise the use of one or more cells, growth factors, grafts (e.g. tissue grafts such as nerve grafts) to aid in tissue regeneration, additional antioxidants, hormones, steroids, vitamins, minerals or a combination thereof to facilitate treatment (healing) of the spinal cord injury.

Examples of cells include stem cells, neuroprogenitor cells, embryonic stem cells, neural stem cells, mesenchymal stromal cells, Schwann cells, induced pluripotent stem cells, neurons or a combination thereof. In the presence of ROS, stem cells either do not survive or differentiate. These cells could be mixed with nano-SOD/catalase to enchance their survival and differentiation into neuronal cells. One could inject a combination of cells and nano-SOD/catalase to facilitate rapid repair of injured spinal cord. Examples of growth factors include brain derived neurotrophic factor (BDNF), neurotrophin-3 (NT-3), acidic fibroblast growth factor (aFGF; FGF-1), hepatocyte growth factor (HGF) or a combination thereof. Examples of additional antioxidants include glutathione peroxidase, glutathione reductase, caspase inhibitors, or a combination thereof. Examples of hormones include one or more thyroid hormones. Examples of steroids include methylprednisolone, beta-estradiol or a combination thereof.

In addition, vitamins such as C, E, A (beta-carotene); nutrients such as lutein, lycopene, vitamin B2, coenzyme Q10; amino acids such as cysteine and herbs such as bilberry, turmeric (curcumin), grape seed or pine bark extracts and ginko can be used.

In particular aspects, the SOD and the catalase encapsulated in the one or more nanoparticles and the cells are mixed in a scaffold (a biocompatible scaffold), such as a hydrogel, prior to or upon administration (e.g., to immobilize the cells and nanoparticles at the site of injury).

The NPs for use in the compositions and methods described herein can be administered in a variety of formulations. In one aspect, the one or more nanoparticles are formulated as a lyophilized powder.

As described herein, the invention is directed to therapies aimed at conditions (e.g., SPI; protection of the spinal cord during a medical intervention), and/or neurodegenerative diseases and/or neuronal injury associated with excessive production of ROS in an individual in need thereof. In one aspect, the therapy ameliorates the symptoms associated with the condition and/or disease in an individual. In other aspect, the therapy arrests the condition and/or disease in the individual. In yet other aspects, the therapy eradicates the condition and/or disease in an individual.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact condition and/or disease to be treated, the severity of the condition and/or disease from which the patient suffers, the chosen route of administration, other drugs and treatments which the patient may concomitantly require, and other factors in the physician's judgment.

An effective amount of SOD and catalase is delivered to an individual in need thereof. As used herein, "effective amount" or "therapeutically effective amount" means an amount of the active compound that will elicit the desired biological or medical response in a tissue, system, subject, or human, which includes alleviation of the symptoms, in whole or in part, of the condition and/or disease being treated.

The composition can be administered in a single dose (e.g., in a day) or in multiple doses. In addition, the composition can be administered in one or more days (e.g. over several consecutive days or non-consecutive days), weeks, months or years.

The compositions provided herein can be delivered in a composition, as described above, or by themselves. They can be administered systemically, or can be targeted to a particular tissue. The therapeutic compounds can be produced by a variety of means, using chemical synthesis; recombinant production; and/or in vivo production.

The invention is also directed to a pharmaceutical composition comprising SOD and catalase encapsulated in one or more NPs. The compounds for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. The pharmaceutical compositions of this invention can also be administered as part of a combinatorial therapy with other compounds. The composition can be administered prior to surgical intervention, during, or following the procedure.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration. It can be administered as a bolus injection.

Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

EXEMPLIFICATION

Example 1

Formulation of Catalase and SOD-Loaded NPs

Materials and Methods
Materials
Poly(D,L-lactide co-glycolide) (PLGA, inherent viscosity, 0.76-0.94 dL/g, copolymer ratio 50:50) was purchased from Lactel (Cupertino, Calif., USA). Polyvinyl alcohol (PVA: average MW 30,000-70,000), L-tartaric acid dimethyl ester (DMT), Catalase from bovine liver, Tween-20, Sodium azide, Bovine serum albumin (BSA) and Rat serum albumin (RSA) were purchased from Sigma-Aldrich Chemical Company (St Louis, Mo.).

Formulation of Nanoparticles
Catalase loaded PLGA-NPs were formulated using a double emulsion solvent evaporation method. Briefly, 81 mg PLGA polymer and 9 mg DMT were dissolved in 3 mL dichloromethane to form a polymer solution. PVA solution was prepared by slowly adding 5 g of PVA in 100 mL of water with stirring on a magnetic stir plate. Temperature of the PVA solution was raised to 85-95° C. to completely dissolve PVA. The PVA solution was cooled to room temperature and then filtered through a 0.22 μM syringe filter (MILLEX® GP Filter unit, Millipore Ireland Ltd, IRL). An aqueous solution of catalase (8 mg, 2000-5000 Units/mg) and 22 mg of RSA in 300 IJL of double distilled water was first emulsified into the polymer solution by vortexing for 1 min, followed by sonication using a micro tip probe sonicator for 2 min on an ice bath at 55 W of energy output (XL 2015 Sonicator® ultrasonic processor, Misonix Inc., Farmingdale, N.Y., USA) to form a primary water-in-oil emulsion. RSA provides stability to the encapsulated enzyme from interfacial inactivation, and DMT facilitate the release of encapsulated enzyme from NPs. The primary emulsion was further emulsified into 18 mL PVA solution first by vortexing and followed by sonication as described above. The secondary, water-in-oil-in-water emulsion, thus formed was stirred overnight on a magnetic stir plate at room temperature followed by stirring in a vacuum desiccator for 1 h to allow complete removal of organic solvent. The resultant NPs were then recovered by ultracentrifugation at 30,000 rpm for 30 min at 4° C. (50Ti Rotor, Beckman Optima LE-80K: Beckman Instruments, Palo Alto, Calif.) and washed twice with water to remove PVA and un-encapsulated proteins by resuspending NPs each time in water followed by sonication and centrifugation as above. The washings were collected and analyzed for the amount of catalase that was not encapsulated in NPs using the amplex red catalase assay kit (Amplex® red catalase assay kit, Molecular Probes, Invitrogen, Oreg.). The final suspension was centrifuged at 1500 rpm for 10 min the supernatant was lyophilized in sterile tubes for two days at −48° C. and vacuum ~0.035 mBar (LABCONCO FreeZone® 4.5 Liter Freeze Dry Systems, Labconco Corporation, Kansas City, Mo.). NPs with 30 mg of RSA without the enzyme were used as control.

Characterization of Catalase NPs
The hydrodynamic diameter and surface charge of NPs were measured by dynamic light scattering (DLS) method at an intensity of 300 kHz using Nicomp™ 380 DLS (Zeta Potential/Particle Sizer, Santa Barbara, Calif., USA). To measure the size, a suspension of NPs (0.5 mg/mL) in water was prepared by sonication using a micro tip probe sonicator as above for 1 min. The same diluted samples were used to measure zeta potential of NPs in phase analysis mode and the current mode at a scattering angle of −14° using Nicomp™.

Catalase Loading Efficiency in NPs
Loading efficiency of catalase in NPs was assessed by an indirect method, i.e. by determining the total amount of catalase added in the formulation and subtracting that which did not get encapsulated. Supernatant and washings collected during the preparation of NPs were assayed for enzyme activity. Quantification of protein loading, as determined by the indirect method, correlates with the total protein released from NPs in vitro (Oyinbo, C A, 2011 Acta Neurobiol Exp (Wars), 71:281-299). Activity of the catalase was measured using Amplex® red catalase assay kit as described above.

In Vitro Release of Catalase from NPs
Catalase release from NPs in vitro was carried out in phosphate buffered saline (PBS) (0.15M, pH 7.4), containing BSA (0.1%), Tween-20 (0.05%) and sodium azide (0.05%) as preservative. The release study was conducted using double diffusion chambers separated a low-protein binding 0.1 μm porosity membrane (Type VV, Millipore Co., Bedford, Mass., USA) as described in earlier studies (Oyinbo, C A, 2011 Acta Neurobiol Exp (Wars), 71:281-299).

Briefly, 6 mg of NPs were dispersed in 7.5 mL of release buffer. The suspension was then vortexed and sonicated in a water bath sonicator (FS-30, Fisher Scientific) for 10 min. The donor side of each chamber was filled with 2.5 mL of the NPs suspension and the receiver chamber with an equal volume of release buffer alone. Since the hydrodynamic diameter of the NPs is greater than the membrane porosity, only the protein will penetrate through the membrane into the receiver chamber. The chambers were placed on a shaker maintained at 37° C. and rotating at 110 rpm. At different time intervals, the solution from the receiver chambers was removed completely and replaced with a fresh buffer. The collected samples were analyzed for catalase activity using the Amplex® red catalase assay kit.

Results

Formulation and Characterization of Catalase Loaded PLGA-NPs

The average of NPs was 280.17±0.246 (n=3) with polydispersity index of 0.034±0.0071. The average zeta potential of the particles was found to be −20.01±0.85 mV (n=3). The control without enzyme also demonstrated almost identical physical properties as the catalase loaded NPs. The encapsulation efficiency of the catalase in NPs was ~99±0.03% (n=4). Each mg of NPs contained ~87 μg (~307 Units) of catalase. The release of catalase from NPs was sustained, with ~24.2±1.3 units/mg of NPs catalase release occurring in ~4 weeks.

SOD-Loaded NP

These NPs were prepared using the identical protocol as used for formulating catalase-loaded NPs. SOD=12 mg and RSA=18 mg were dissolved in 300 μl water prior to emulsification in PLGA solution as above.

Described herein is the use of SOD and CAT in a nanoparticle (NP) formulation for treating SPI and neurodegenerative diseases. Dismutation of superoxide leads to formation of H2O2, which if not neutralized by catalase, can be damaging to cells and tissue. SOD and catalase are known to be active scavengers of free radicals where SOD catalyzes the dismutation of superoxide radicals to oxygen and hydrogen peroxide, and catalase further catalyzes the decomposition of hydrogen peroxide to water. The enzyme levels of SOD and catalase are significantly reduced after SPI and hence an efficient transportation system as described herein, supplements the function of these scavenging enzymes and averts the formation of ROS, reducing the overall spread of the secondary injury. A combination of these two enzymes can exert a synergistic neuroprotective effect, and thus, provide the necessary protection from ROS-induced damage. Furthermore, H2O2 acts as a signaling molecule for the recruitment of leukocytes to the injured site; thus its neutralization with catalase prevents their infiltration of the damaged area and the resulting inflammatory response.

Animal Model

An animal model for traumatic SPI was developed, tested and evaluated using Nano-SOD/catalase. Adult male Sprague-Dawley rats (200-300 g) were anesthetized and their spinal cords were exposed by laminectomy at the level of the T9/T10 vertebrae. Body temperature was monitored with a rectal thermometer and maintained at 36.4° C. using a heating pad. The animal was put in an induction chamber with Isoflurane maintained at 2-3%. Once the animal was deeply sedated, the surgical field was shaved from the shoulders to the hips. 2 cc of normal saline was injected intraperitoneally to keep the animal well hydrated and a lubricating eye gel was applied to protect the eyes during the procedure. Reference markers were drawn on the animal perpendicular to the vertebral column at the front legs and hind legs. The interior of these markers were subdivided into thirds so that there was an upper, medial, and lower portion demarcated along the vertebral column. The animal was placed in a prone position and the surgical site was swabbed with 10% Betadine solution, working from the interior to outside. Antiseptic was allowed to remain on the skin for 3 minutes in order to act on surface bacteria before an incision was made. The animal was then fixed to a stereotaxic frame (KOPF) using a transverse bar and silk suture. The animal was covered with sterile surgical drape leaving only the surgical site exposed. An incision was made at 1 cm below the union of upper and middle marked segments. Using a disposable scalpel, a longitudinal incision of 2.5 cm was performed on dorsal side of animal down the vertebral axis. This ensured access to vertebrae T13 through L3 on the animal. The dissection was performed by planes along the spine, detaching the spinotrapezium muscle from bone, using scissors. Tissues were retracted using hemostats to allow easy access to the vertebral column and spinal cord. Using a Leica dissection microscope to aid in visualization, a complete laminectomy was performed, with removal of the pedicles by using a dental drill (Microlab) and bone nibbler, in order to allow an extradural application of weight compression with minimal displacement of the spinal cord. A spinal cord contusion injury was induced onto the exposed spinal cord by utilizing a Kopf weight drop spinal compression apparatus with a 10 g weight dropped from a height of 25 mm (severe) onto the laminectomized cord. Wound site was closed with 3-0 Monoacryl absorbable monofilament suture and reverse cutting ⅜ curve needle, using interrupted stitches, taking care not to over tighten the stitches. The animal was closely monitored after the surgery while recovering from anesthesia. For pain management, buprenorphine at 0.05 mg/kg was given immediately after surgery, 6-8 h post-op, twice at 6-8 h the day after the surgery, and then up to 3 times daily if necessary. Animals had their bladders expressed manually twice daily for one week post-surgery and then once daily thereafter in order to prevent urine retention. The treated animals were housed in cages with soft bedding with food and water accessible from bottom of cage. Animals were weighed weekly to ensure no significant weight loss occurs.

Figure 2:
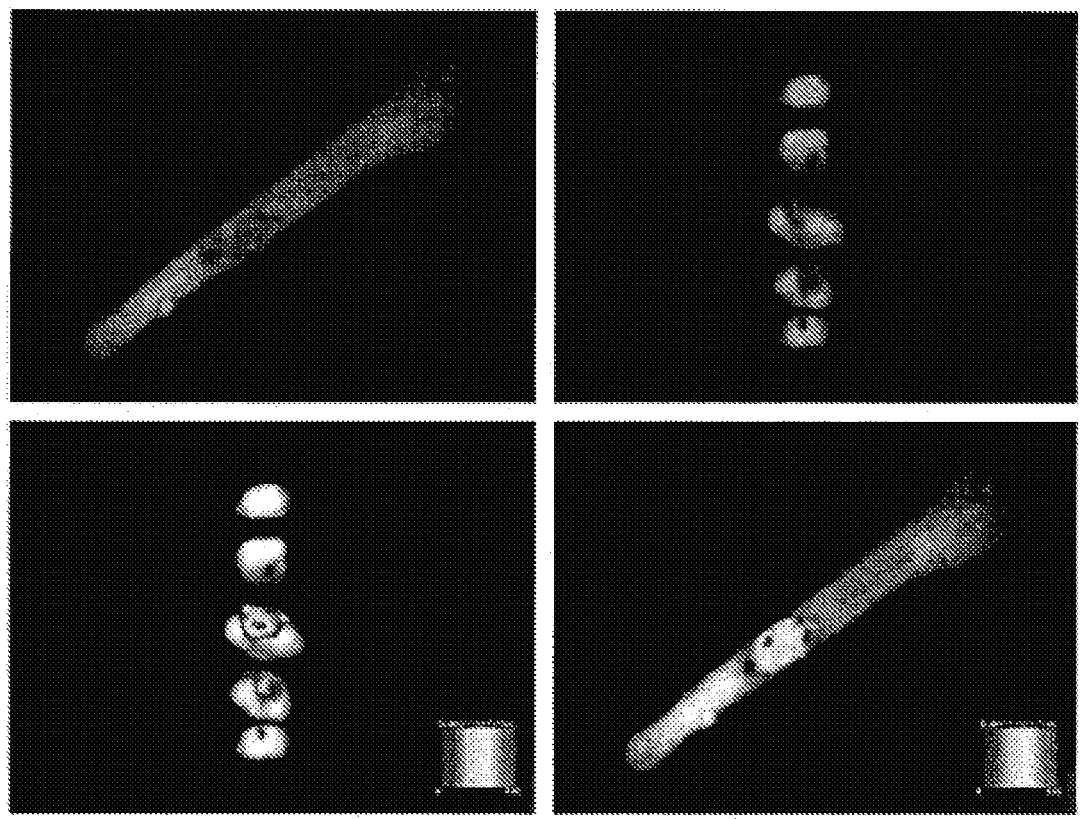
FIG. 2 shows nanoparticle localization in the injured segment of spinal cord where nanoparticles are injected via carotid artery. In this procedure, a catheter is guided from the carotid artery to the heart ventricle for administration of nanoparticles.

Nanoparticles Delivery & Localization at the site of the lesion: The initial experiments were aimed at determining the localization and quantification of NPs at the damaged lesion site in case of a spinal cord injured animal. For this study, NPs were loaded with a near-infrared (NIR) dye (S085700, H W Sands, Jupiter, Fla.), and administered through two different routes: a) intra-arterial via carotid artery (IA) via the common carotid artery (CCA) to the ventricle so that the injected NPs directly go into the blood supply that goes to the spinal cord and b) intravenous (IV) route via the tail vein, both routes were tested 3 hours after the injury induction procedure. For quantification purposes, a standard curve was generated using dye loaded NPs and the signal intensity was found to be proportional to the amount of dye accumulated. Animals were euthanized after 24 h and the NPs accumulated at the site of the lesion were quantified. Results from these experiments indicated no significant difference between the quantities of the accumulated NPs via IA and IV routes, prompting the continuation of studies with the IV route of administration, a relatively easier and a clinically more viable procedure. See FIGS. 1 and 2.

Each 1 mg PLGA nano particle was loaded with 581 units SOD=1271 μg

Each 1 mg PLGA nano particle was loaded with 311 units Cat=881 µg

The concentration of the suspension used for injection of the animal is 1 mg/100 µl (10 mg/ml). It was considered that the average animal weight was 350 g, dose of Catalase NPs=5.25 mg (525 µl suspension) SOD-loaded NPs=1.7 mg (170 µl suspension). Total volume of suspension is 695 µl for a 350 g animal). Each formulation of NPs is loaded in different sterile syringe (1 ml syringe), NPs are injected over 1 minute; first catalase-loaded NPs, then 100 µl saline and then SOD-loaded NPs (total duration of injection was about 3 minutes). For the purpose of injection, animals were anesthetized with isoflurane, tail was cleaned with alcohol pad, 26 gage intra venous catheter was inserted for NP injection as described above.

Locomotor Testing

SPI is known to severely debilitate the motor system in affected populations causing grave impairments in ordinary locomotion. The hind limbs are mostly affected causing either paraplegia, quadriplegia and in some cases even complete paralysis of the lower limbs. These tests help to certify and document the recovery that ensues post-treatment. To assess the therapeutic efficacy of the nano-SOD/CAT therapy on the locomotor functions, the Basso, Beattie and Bresnahan (BBB) test was conducted.

Figure 3:
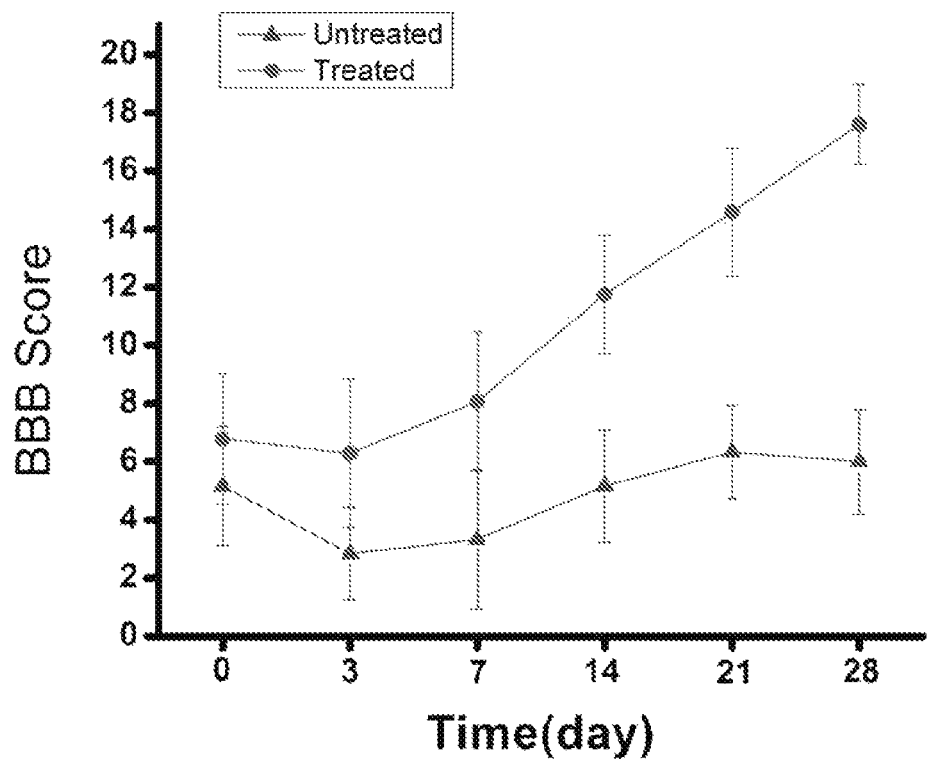
FIG. 3 shows graphs of Basso, Beattie and Breshnahan (BBB) neurological scoring. Treated animals show significant improvement in locomotive functions at 28 days as evident from their higher BBB score than untreated animals.

The BBB scale is a widely accepted and used rating scale that allows for standardization of outcomes across similar SCI research. The BBB scoring is conducted at different time points after the initiation of SCI. To acutely assess the recovery pattern post-SCI, scores range from 0, indicating complete paralysis, to 21, indicating normal locomotion. It provides investigators with a very judicious evaluation of the motor abilities of an injured animal by appraising the limb and joint movements. Parameters assessed include the ability at weight support, limb coordination, foot placement and gait stability. See FIG. 3.

Figure 4:
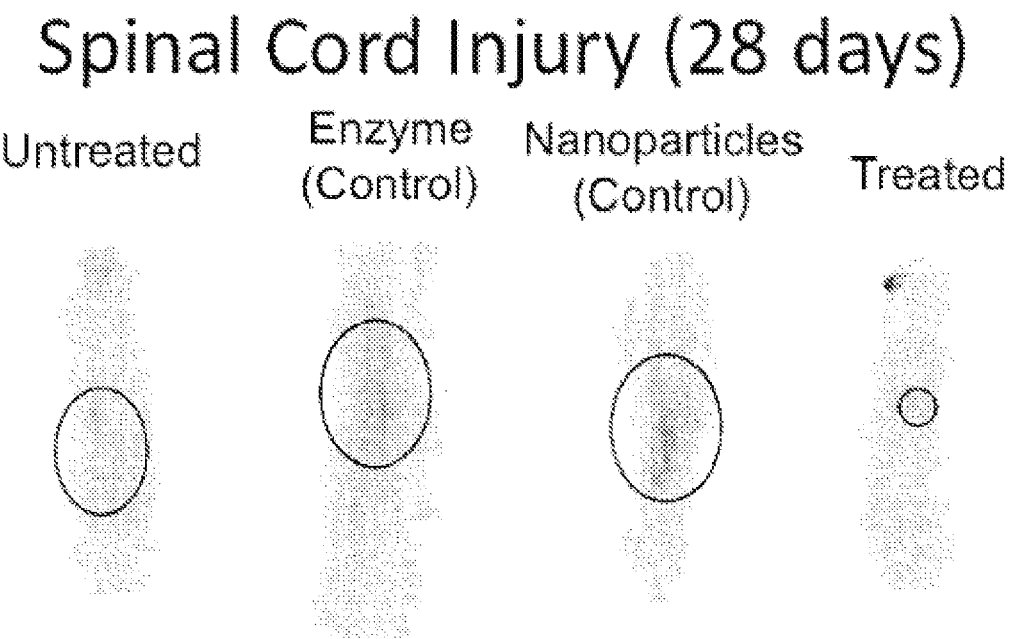
FIG. 4 shows healing of the injured spinal cord from treated animals compared to untreated animals at 28 days. Enzyme alone or nanoparticles without enzymes (Controls) do not show healing.
Figure 5:
FIG. 5 shows histological analysis of injured spinal cord at 28 days. Treated animal shows significant healing of the lesion site as compared to untreated animal.
Figure 5:
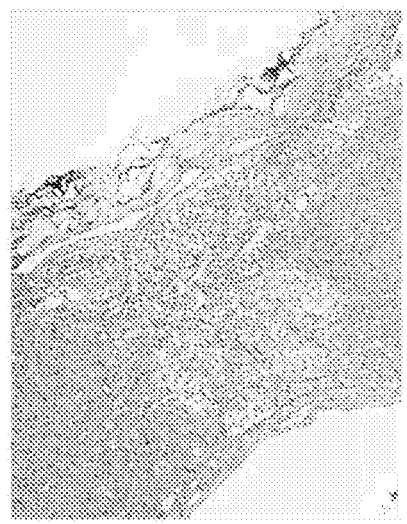

In untreated animals there is severe tissue damage, multiple cavitations (syringomyelia), severe neuronal tissue loss with prominent tissue necrosis and poor healing process 28 days after SCI. In treated animals there is wedge shape SC lesion, there is less cavitations, very small syringomyelia, less neuronal tissue loss, less tissue necroses and evidence of good tissue healing 28 days after SCI. See FIGS. 4 and 5.

Figure 6:
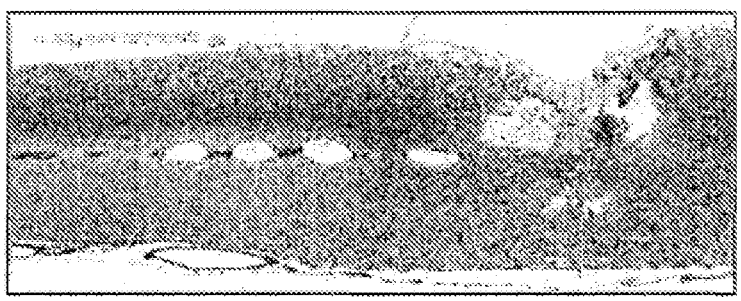
FIG. 6 shows the extent of syringomyelia (cavitations) in treated and untreated animals. Treated animals do not show cavitation.
Figure 6:
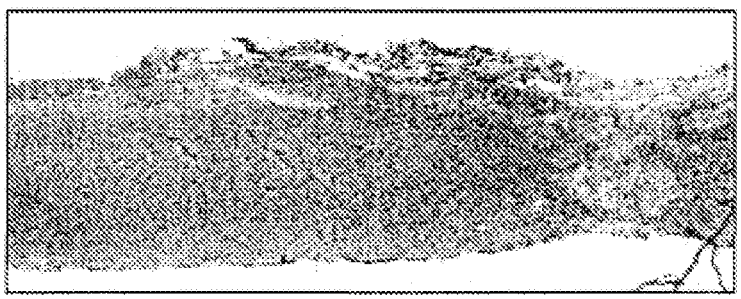

Syringomyelia is a generic term referring to a disorder in which a cyst or cavity forms within the spinal cord. These are fluid filled holes in the spinal cord. This cyst, called a syrinx, can expand and elongate over time, destroying the spinal cord. The damage may result in pain, paralysis, weakness, and stiffness in the back, shoulders, and extremities. Syringomyelia may also cause a loss of the ability to feel extremes of hot or cold, especially in the hands. The disorder generally leads to a cape-like loss of pain and temperature sensation along the back and arms. Each patient experiences a different combination of symptoms. These symptoms typically vary depending on the extent and, often more critically, to the location of the syrinx within the spinal cord. FIG. 6 shows inhibition of syringomyelia in treated animals.

Figure 7:
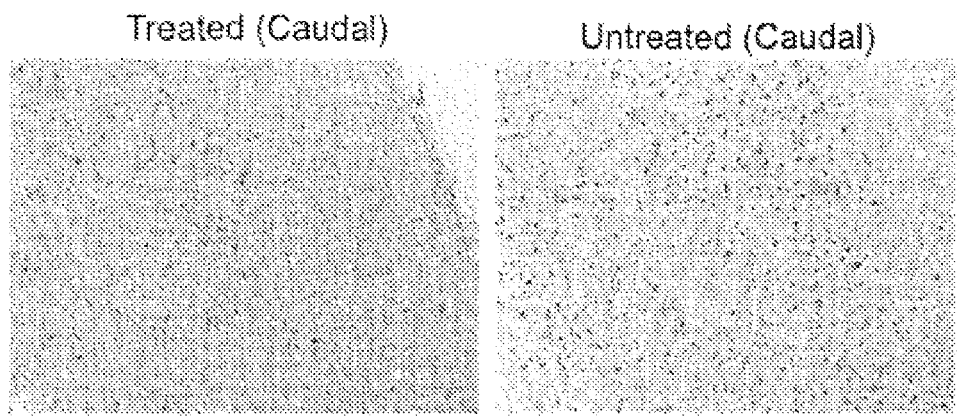
FIG. 7 shows reduced caspase activity (apoptosis) in caudal (below the injured site) section of the spinal cord in treated as compared to untreated animals. The level in treated animals is the same as in a normal spinal cord.

As shown in FIG. 7, caspase activity (apoptosis) in the caudal section of spinal cord was reduced in treated animals compared to untreated animals.

Figure 8:
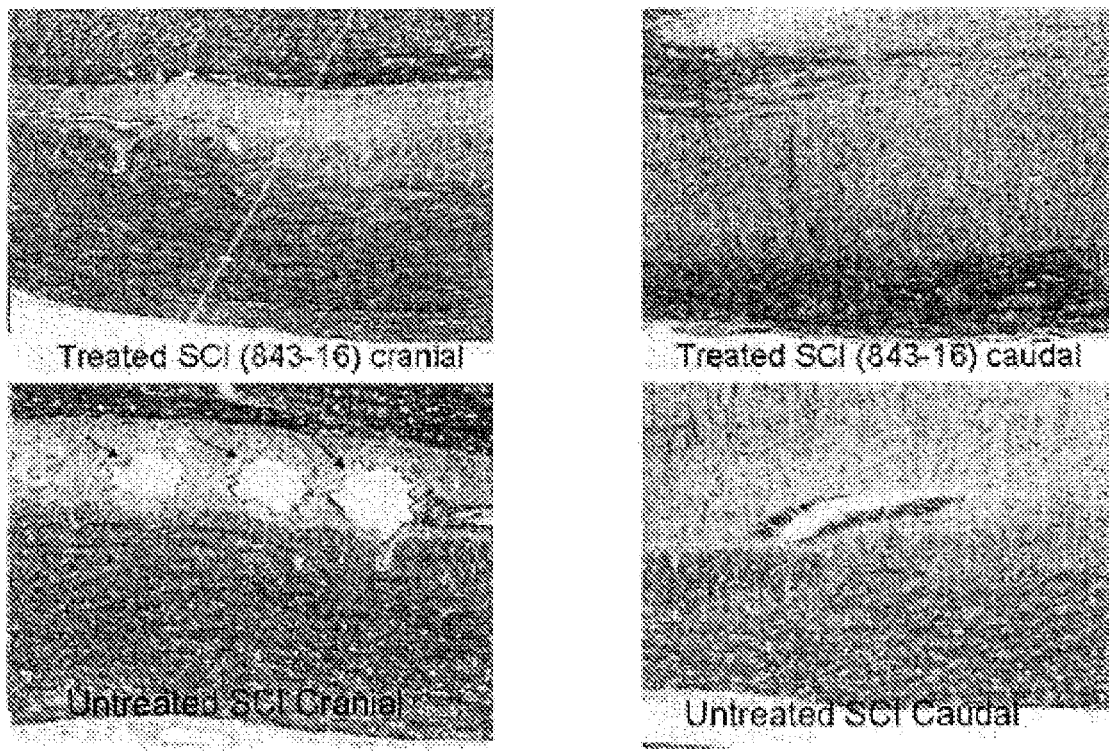
FIG. 8 shows demyelination in caudal spinal cord of untreated animals but not in the spinal cord of treated animals.
Figure 9:
FIG. 9 shows migration of microglia, which play a role in the repair process of treated animals. Results of treated animals 6 days post SCI and treated animals 4 weeks post SCI are shown. There were a lot of Iba1 positive cells in lesion epicenter at 6 days post SCI. Most of the Iba1 expression in the epicenter/lesion was gone by 4 weeks. An increase in Iba1 expression outside of epicenter/lesion was seen in the untreated rats (but not much of an increase in untreated rats) compared to naïve.
Figure 9:
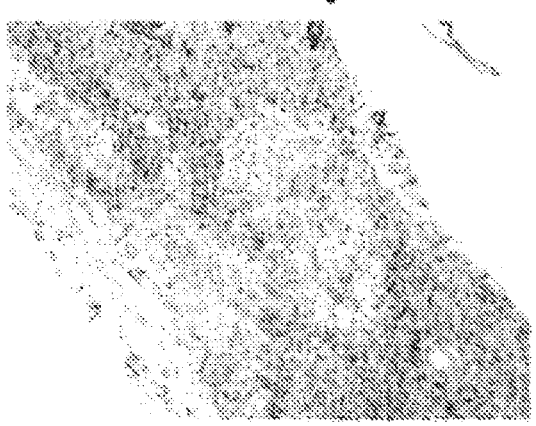

Demyelination is one of the important pathological consequences of SCI and is caused due to the loss of the protective sheath of myelin by a steady decrease in the number of oligodendrocytes destroyed by apoptosis and or necrosis. Remyelination that naturally occurs after the injury helps to restore the lost signal conduction and transmission, but is usually abnormal in nature. Partial primary demyelination typically starts within the first day of the injury and peaks at 3 weeks after the injury. FIG. 8 shows demyelination in caudal spinal cord of untreated animals but not in the spinal cord of treated animals. FIG. 9 shows migration of microglia in the treated animals.

Inhibition of Collagen Synthesis in Treated Group

Figure 10:
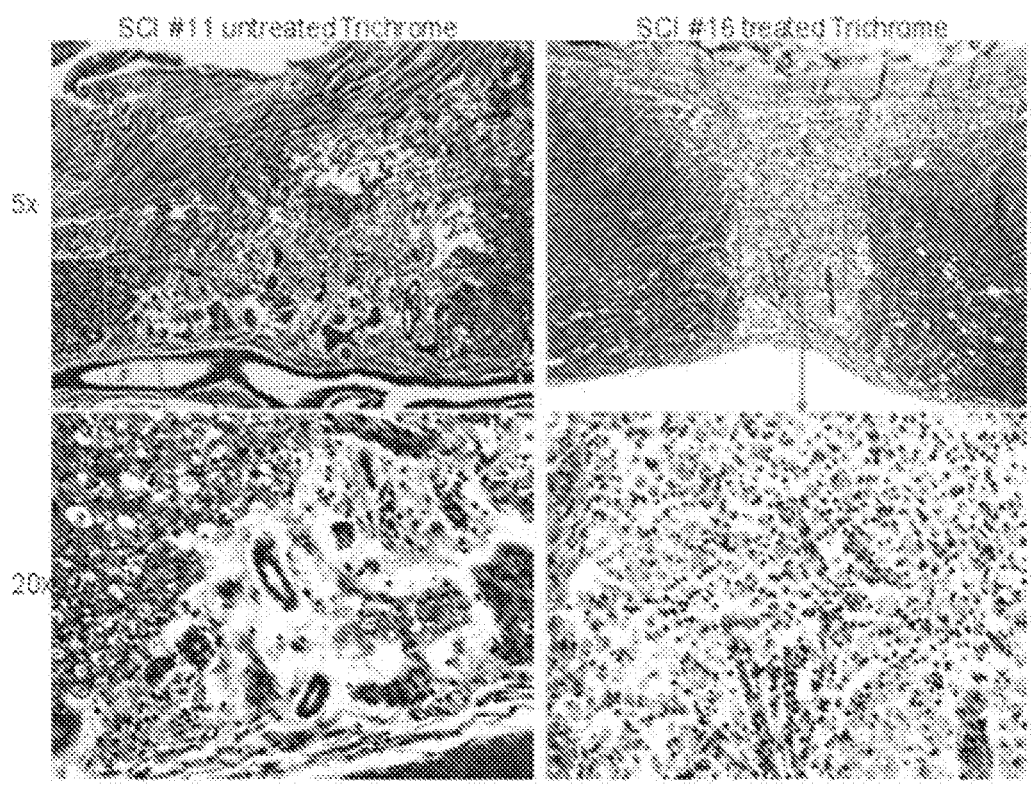
FIG. 10 shows inhibition of collagen synthesis at the lesion site in treated animals. Collagen is a major component of scar tissue that is usually formed following spinal cord injury which inhibit axonal growth and neural connectivity.

Collagen, one of the extra cellular matrix proteins, is a very suitable marker for the "anatomical scar", it is not normally found in the spinal cord but can be seen in the lesion site post spinal cord injury. Here we show that treated animals do not show collagen deposition whereas untreated animal show significant deposition of collagen (blue color) at the injured site. Scar tissue prevents axonal growth and neuronal connectivity. Spinal cord sample collected at 28 days. Representative figure from 4-5 animals (treated or untreated). See FIG. 10.

Collagen is a major component of scar tissue. A shown in FIG. 9, the treatment group collagen synthesis at the impacted site (at 28 days) was significantly less than in the untreated group. Scar tissue prevent axonal growth and hence neuronal connectivity.

Conclusion

As shown herein, the nano-SOD/catalase can be used, for example, as an intravenously injectable delivery system, using FDA-approved biodegradable polymer-based nanoparticles (NPs) containing stabilized anti-oxidant enzymes (superoxide dismutase (SOD) and catalase). As will be appreciated by those of skill in the art, one preparation of NPs loaded with SOD and catalase, or two separate formulations can be used, one loaded with SOD and other with catalase. In one aspect, the treatment can be performed by injecting first catalase-loaded NPs, saline, and then immediately SOD-loaded NPs. The methods provided herein are exemplified using a single-dose intravenous injection of nano-SOD/catalase 3 hr following SPI in rats. Considering that the metabolic activity in humans is significantly lower than in rats (~20 times), this therapy is likely effective in humans after within minutes or hours following SPI.

Typically the primary injury to the spinal cord occurs as a direct impact of the mechanical force on the spinal cord followed by the secondary injury, which is usually accompanied by changes in the pathophysiological aspects of the spinal tissue. While it is impossible to forestall the primary injury, as shown herein, the secondary injury, which is more progressive in its path, provides a therapeutic window to treat and prevent the further extension the secondary damage. However, reactive oxygen species (ROS) formation occurs as a consequence of the secondary injury and continues to escalate and intensify the secondary injury process by causing enormous damage to cells, DNA, lipids, proteins and eventually causing cell death. At present, no effective neuroprotective pharmacological treatment exists that can prevent, minimize or halt the progression of such a protracted and devastating injury. Nano-SOD/catalase can impede the formation of ROS and provide continual neuroprotection from ROS. The course of action of the nano-SOD/catalase can be localized in the spinal tissue followed by initially rapid and later slow release of the encapsulated enzymes over a sustained period of time, if desired. This gradual and steady release of beneficial enzymes can prevent auxiliary degeneration of the spinal tissue and avert subsequent motor function deterioration. It can also create favorable conditions to allow the natural repair mechanisms of the spine to restore and heal the impaired areas, allowing for an improved recovery of physiological, psychological and behavioral aspects of the affected individual.

Currently, no pharmacological treatment exists that can prevent, minimize or halt the progression of the secondary injury. Various cellular and molecular therapies are being investigated but rehabilitative therapy remains the only effective route in assuaging the pain and trauma associated with SPI. Immediate treatment of SPI involves surgical decompression and/or stabilization of the vertebrae to control the primary injury. It is argued that decompression surgery performed within 24 hrs following trauma leads to improved neurological recovery than those performed after 24 hrs. However, delivery of expedient surgical care often pose barrier in a trauma setting. The decompression procedure does not repair the already injured spinal cord but is aimed at minimizing further progression of the secondary damage.

Systemic high dose of methylprednisolone, an intravenous steroid, has been registered for use in clinical trials for SPI by the FDA. Even though the treatment boasts of a modest recovery after SPI, the overall risks, including sepsis, gastric bleeding, pneumonia, wound infection and increased susceptibility to an auto-inflammatory response, render it controversial in nature.

Moderate hypothermia has been shown to be protective in a variety of preclinical studies but clinical studies were inconclusive because of small sample size and lack of a randomized controlled study. Systemic hypothermia could cause complications related to hypothermia including infection, acute respiratory distress syndrome, pneumonia, venous thrombosis, etc. This occurs because of the impaired platelet functions at lower body temperature.

Other research approaches include cellular grafts including segments of peripheral nerves grafts, transplantation of Schwann cells, olfactory ensheathing glia, neuronal progenitor cells, stem cells, fibroblasts, marrow stromal cells. However, most of the transplanted cells do not survive and/or differentiate to provide significant benefits.

In one aspect, the compositions and methods described herein provide for therapy post-SPI; however, in other aspects, nano SOD/catalase can also be used to treat already injured spinal cord patients. Scar tissue formation at the injured site is the major problem that impedes regeneration of neurons and axonal connectivity. One solution is to dissect out the scar tissue and treat the incision site with nano-SOD/catalase to facilitate regeneration. The methods and compositions provided herein can further comprise the use of stem cells or neuronal progenitor cells with nano-SOD/catalase to facilitate neuronal repair. ROS at the injured site are detrimental to the transplanted cells and hence they do not survive or differentiate. Nano-SOD/catalase can neutralize ROS to protect the transplanted cells and facilitate their differentiation. In a particular aspect, cells and nano-SOD/catalase are combined in a scaffold (e.g., hydrogel) to immobilize the therapy at the treatment site.

Further, nano-SOD/catalase can be used to treating other neurodegenerative diseases, particularly those that are implicated due to excessive production of ROS such as Parkinson's disease (PD), Alzheimer's disease (AD), Multiple Sclerosis (MS) and amyotrophic lateral sclerosis (ALS). Nano-SOD/catalase could potentially be used for treating other neuronal injures.

Shown herein, nano-SOD/catalase can be formulated using a FDA approved biodegradable and biocompatible polymer. Final formulation can also be a lyophilized powder, which can be easily reconstituted for intravenous injection. It is feasible for paramedics at the site to inject nano-SOD/catalase based on the initial assessment of the victim. Since these antioxidant enzymes are present in the body, injection of nano-SOD/catalase is not expected to cause any side effects but to provide protective effect from further aggravating the damage. One could also inject nano-SOD/catalase prior to patients undergoing full diagnosis and surgical decompression procedure.

High doses of methylprednisolone, which is currently used drug in SCI patients, causes serious side effect and its efficacy is also questionable. Local hypothermia requires surgical intervention whereas systemic hypothermia causes serious complications. Both show marginal improvement in recovery. Cell-based therapy is under investigation. In summary, there is no treatment available to partially or completely regenerate injured spinal cord.

The imaging study with near-infrared dye-loaded nanoparticles shows localization of nanoparticles in the injured segment of spinal cord following their intravenous injection. Nanoparticles were injected three hrs following spinal trauma through tail vein and the spinal cord was harvested 24 hr following nanoparticle injection for imaging. In another study, nanoparticles were injected through carotid artery to test whether this route results in more efficient delivery of nanoparticles in the injured segment than intravenous injection. However, the imaging data do not show significant difference and hence the future efficacy studies were carried out via intravenous injection of nano-SOD/catalase.

Efficacy of nano-SOD/catalase is demonstrated in a rat model of traumatic spinal cord injury. Animals treated with nano-SOD/catalase show significantly higher Basso, Beattie and Bresnahal 1 (BBB) score than controls (no treatment, enzymes alone, or nanoparticles without enzymes). BBB score represents locomotor functions on the scale from complete paralysis (score 0) to normal locomotion (score 21). Treated animals show BBB score improvement from average 7 (day of surgery) to 18 in four weeks whereas untreated animals show no improvement in the BBB score. Treated animals also gain more weight than untreated animals and also they look very active. Histological analysis of spinal cord after four-weeks shows significant healing of the injured spinal cord in treated animals whereas the spinal cord of untreated animals shows several cavities. Post-traumatic syringomyelia and tethered spinal cord can occur following SPI. It can occur from two months to many decades after injury in humans. The results can be devastating, causing new levels of disability long after a person has had successful rehabilitation. The clinical symptoms can include progressive deterioration of the spinal cord, progressive loss of sensation or strength, profuse sweating, spasticity, pain and autonomic dysreflexia. Shown herein is that animals treated with nano-SOD/catalase do not develop syringomyelia whereas untreated animals do even at four weeks.

Mechanistic studies: In treated animals, caudal part (below the injury) of the spinal cord shows significantly few cells with apoptosis (same number as in naive animals) whereas untreated animals apoptotic cells are significantly more in number. Similarly, there is greater demyelination of neurons in caudal spinal cord in untreated animals whereas there appears no demyelination in treated animals. These results suggest that nano-SOD/catalase prevents degeneration of neurons because of the connectivity between the caudal and cranial parts (below and above the injured site) of the spinal cord. Demyelination is the term used for a loss of myelin, a substance in the white matter that insulates nerve endings. Myelin helps the nerves receive and interpret messages from the brain at maximum speed. When nerve endings lose this substance they cannot function properly, leading to patches of scarring, or 'sclerosis', occurring where nerve endings have lost myelin. Demyelination is also the cause of multiple sclerosis.

Mechanism of Repair: This is aimed at determining which cells migrate at the injured site and their role in the repair process. Preliminary results show migration of microglia filling the trauma site as early as 6 days post injury; however, no microglia are seen at the injured site at 28 days. Microglia are the primary mediators of the central nervous system's (CNS) immune defense system and are integral to the subsequent inflammatory response. Whether microglia are 'good' or 'bad' is under debate, with strong support for a dual role or differential activation of microglia. Without wishing to be bound by theory, it is believed that in the absence of ROS, they clear cellular debris and maintain normal cellular homeostasis, thereby preserving and protecting healthy tissue. In the presence of ROS, such as in untreated animals, microglia may not be able to perform the above function. Microglia produce a number of neuroprotective substances in response to injury, such as anti-inflammatory cytokines and neurotrophic factors, including nerve growth factor (NGF), transforming growth factor β (TGF β), IL-IO, and IL-1 receptor antagonist (IL-1 ra). Also shown herein is inhibition of scar tissue (collagen) in the injured tissue in treated group whereas untreated animals show presence of collagen.

Example 2

Nanoparticle Formulation Containing SOD and Catalase Together

In a typical procedure, 12 mg SOD, 8 mg catalase, 18 mg rat serum albumin were dissolved in 300 µl water which was then emulsified in 3 ml PLGA (90 mg PLGA, intrinsic viscosity=0.76-0.94 dL/g) solution in dichloromethane which also contained 9 mg dimethyl tartaric acid. This emulsion was further emulsified in 18 ml 5% polyvinyl alcohol solution. Following evaporation of organic solvent, nanoparticles were recovered by ultracentrifugation, washed, and lyophilized. Mean hydrodynamic diameter of these nanoparticles was 323 nm with polydispersity index 0.011 and zeta potential of −18.12 mV.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a spinal cord injury in an individual in need thereof comprising:
administering intravenously an effective amount of superoxide dismutase (SOD) and catalase to the individual in need thereof,
wherein the superoxide dismutase and the catalase are encapsulated in one or more nanoparticles that localize at the spinal cord injury and release the SOD and the catalase upon administration,
wherein the nanoparticles comprise poly (D,L-lactide co-glycolide) (PLGA) and polyvinyl alcohol;
wherein the spinal cord injury is caused by a sudden fall, a vehicle accident, sports, or violence, and results in impact of mechanical force on the spinal cord that causes hemorrhage as a consequence of a primary injury and damages spinal cord tissue, and
whereby the individual is treated for the spinal cord injury.

2. The method of claim 1, wherein the SOD and the catalase are encapsulated in separate nanoparticles.

3. The method of claim 1, wherein each of the nanoparticles comprise the SOD and the catalase.

4. The method of claim 1, wherein the SOD and the catalase are administered simultaneously to the individual.

5. The method of claim 1, wherein first the catalase is administered to the individual, then the SOD is administered to the individual.

6. The method of claim 1, wherein the one or more nanoparticles are biodegradable.

7. The method of claim 1, wherein each milligram of nanoparticles comprising the SOD is loaded with about 10 µg to about 150 µg SOD.

8. The method of claim 1, wherein each milligram of nanoparticles comprising the catalase is loaded with about 10 µg to about 150 µg catalase.

9. The method of claim 1, wherein after administration, some of the SOD and some of the catalase are released rapidly from the one or more nanoparticles, and then the SOD and the catalase that remains in the one or more nanoparticles is released slowly over a sustained period of time.

10. The method of claim 1 further comprising administering one or more cells, growth factors, tissue grafts, antioxidants, hormones, steroids, vitamins, minerals or a combination thereof to facilitate treatment of the spinal cord injury.

11. The method of claim 1, wherein the one or more nanoparticles are formulated as a lyophilized powder.

12. The method of claim 1, wherein the SOD and the catalase are administered upon or after removal of scar tissue from the spinal cord injury in the individual.

13. The method of claim 1, wherein the individual is a human.

14. The method of claim 1, wherein the spinal cord injury is caused by said sudden fall.

15. The method of claim 1, wherein the spinal cord injury is caused by said vehicle accident.

16. The method of claim 1, wherein the spinal cord injury is caused by said sports.

17. The method of claim 1, wherein the spinal cord injury is caused by said violence.

18. The method of claim 1, wherein said administering is performed by a paramedic.

* * * * *